United States Patent [19]

Philippson

[11] 3,931,154

[45] Jan. 6, 1976

[54] PROCESS FOR THE PREPARATION OF STEROID OXIRANES

[75] Inventor: Rainer Philippson, Bergkamen, Germany

[73] Assignee: Schering Aktiengesellschaft, Berlin & Bergkamen, Germany

[22] Filed: July 2, 1974

[21] Appl. No.: 485,099

[30] Foreign Application Priority Data

July 7, 1973 Germany............................ 2335154

[52] U.S. Cl.. 260/239.55 R; 260/397.2; 260/239.57
[51] Int. Cl.² ........................................... C07J 17/00
[58] Field of Search ............... 260/239.55, 239.55 R

[56] References Cited
OTHER PUBLICATIONS

Canad. J. Chem. 50 (1972) p. 1414.
J. Prakt. Chem. 314 (1972) p. 667.

*Primary Examiner*—Elbert L. Roberts
*Attorney, Agent, or Firm*—Millen, Raptes & White

[57] ABSTRACT

Steroids containing both an isolated and an $\alpha,\beta$-unsaturated keto group are selectively reacted with dimethyl sulfonium methylide in a non-reactive polar solvent and in the presence of an alkali tertiary alcoholate to produce $\alpha,\beta$-unsaturated keto steroids containing the group

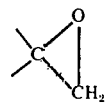

10 Claims, No Drawings

PROCESS FOR THE PREPARATION OF STEROID OXIRANES

BACKGROUND OF THE INVENTION

This invention relates to a process for the production of steroid oxiranes.

Reactions of keto steroids with dimethyl sulfonium methylide to corresponding steroid spiro oxiranes are known per se. "J. prakt. Chem." 314 (1972) 667. However, special precautionary measures must be taken for the production of steroid spiro oxiranes containing an $\alpha,\beta$-unsaturated keto group.

Jones et al. (Canad. J. Chem. 50 (1972) 1414) protect a $\Delta^4$-3-keto grouping by ketalization before the reaction of the 17-keto group with dimethyl sulfonium methylide.

It is an object of this invention to provide a selective process for the production of steroid oxiranes containing an $\alpha,\beta$-unsaturated keto group.

SUMMARY OF THE INVENTION

According to this invention, a steroid containing a spiro oxirane group and an $\alpha,\beta$-unsaturated keto group are produced by reacting a polyketo steroid having an isolated keto group and an $\alpha,\beta$-unsaturated keto group with dimethyl sulfonium methylide in an aprotic polar solvent in the presence of an alkali metal alcoholate, preferably a sodium or potassium alcoholate, of a tertiary alcohol.

DETAILED DISCUSSION

It is surprising that isolated keto groups react selectively according to the process of this invention with dimethyl sulfonium methylide, whereas keto groups which are conjugated with a C=C double bond are not affected, especially since it is known, from the basic research by Corey et al. (J. Am. Chem. Soc. 87 (1965) 1353) that, during the reaction of $\Delta^4$-3-keto steroids, such as, for example, 4-cholesten-3-one, with dimethyl sulfonium methylide, the corresponding oxirane, 4-cholestene-3$\beta$-spiro-1',2'-oxirane, is obtained in a 90% yield.

The products of this invention are $\alpha,\beta$-unsaturated keto steroids of the formula

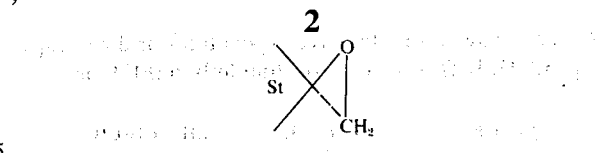

wherein St is a steroid moiety containing an $\alpha,\beta$-unsaturated keto group. They are produced from polyketo steroids of the general formula $$St > = O$$

wherein St has the value given above.

The oxirane grouping can replace an isolated keto group at any desired place in the steroid molecule. If the starting steroid contains more than one isolated keto group, the corresponding polyoxirane steroids are formed. Preferred starting steroids are those having an isolated keto group at one or more of the 3, 6, 11, 12, 17 and/or 20 carbon atoms, e.g., 3-keto, 17-keto, 3,20-diketo, 3,11,20-triketo, 20-keto, 11,20-diketo, 3,12,20-triketo. The $\alpha,\beta$-unsaturated keto group in the starting steroid molecule can be, for example, a $\Delta^4$-3-keto, $\Delta^{1,4}$-3-keto, $\Delta^{4,6}$-3-keto, $\Delta^{1,4,6}$-3-keto, $\Delta^7$-6-keto, $\Delta^{9(11)}$-12-keto, or $\Delta^{16}$-20-keto group. The starting steroid can be, for example, of the estrane, androstane, pregnane, or 19-nor-pregnane natural or synthetic series, e.g., lacking a 13-methyl group or having an 18-methyl group. In addition, the steroid molecule can be substituted with other substituents which are inert with respect to the reactants. Examples are free or functionally modified (e.g., esterified or etherified) hydroxy groups, e.g., alkoxy of 1-4 carbon atoms, benzyloxy, tetrahydropyranyloxy, alkanoyloxy, aryloxy, e.g., benzoyloxy, and aralkanoyloxy, e.g., phenylacetoxy, of at -12 carbon atoms, et the 1-, 3-, 11-, 14-, 16-, 17- and/or 21-positions; alkyl groups of 1-4 carbon atoms, preferably methyl, at the 1-, 6-, 7-, 16-, 17- and/or 18-positions; halogen atoms, e.g., fluorine, at the 6- and/or 9-positions, chlorine at the 6-, 9- and/or 21-positions; and methylene at the 1,2-, 6,7-, or 15,16-position. In addition to the $\alpha,\beta$-unsaturated keto groupings, the steroid molecule can also contain isolated double bonds, e.g., in the 5-, 8-, 9(11)-, 11-, 14- and/or 15-positions.

Examples of such steroids are those of the general formula I

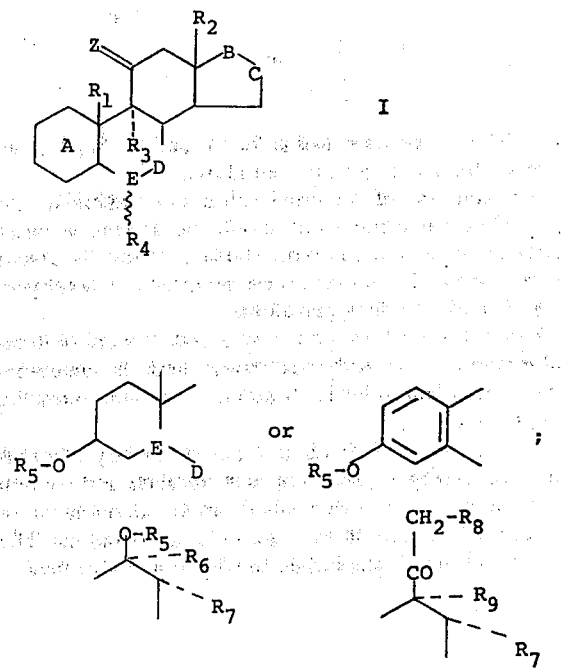

wherein A is

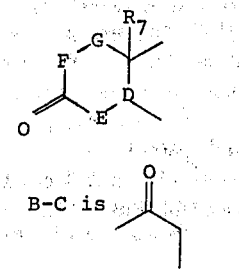

B-C is

Z is an oxygen atom, two hydrogen atoms or the grouping H,OH; E-D is a single or double bond; F-G is

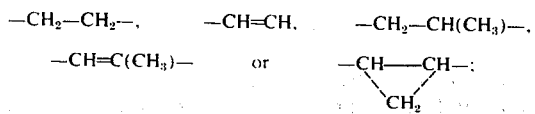

R is a hydrogen atom or methyl; $R_2$ is methyl or ethyl; $R_3$ is a hydrogen, fluorine or chlorine atom; $R_4$ is a hydrogen, fluorine or chlorine atom or methyl; $R_5$ is a hydrogen atom or alkanoyl of up to 15 carbon atoms; $R_6$ is a hydrogen atom, methyl or ethinyl; $R_7$ is a hydrogen atom, methyl or $-O-R_5$; $R_8$ is a hydrogen atom, a halogen atom or $-O-R_8$; $R_9$ is a hydrogen atom or $-O-R_5$; $R_6$ and $R_7$ or $R_7$ and $R_9$ collectively are

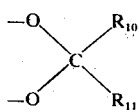

wherein $R_{10}$ and $R_{11}$ each are a hydrogen atom or alkyl of up to 5 carbon atoms, with the proviso that one of A and BC comprises a non-conjugated keto group, preferably BC, and the other an $\alpha,\beta$-unsaturated keto group.

Preferred steroids of Formula I are, inter alia, 3,17-diketo and 3,20-diketo steroids, optionally containing a further keto group at the 11-position, especially those of the general Formula II

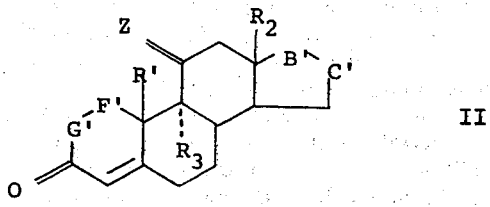

wherein B'C' is

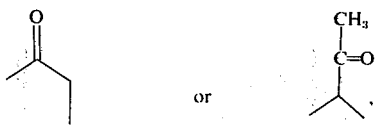

F' - G' is a single or double bond, and $R_1$, $R_2$, $R_3$, and Z each have the values given above.

The amount of dimethyl sulfonium methylide employed is not critical but should be at least a molar equivalent calculated on the starting steroid. To ensure optimum yield, a molar excess preferably is employed, e.g., 0.1 to 5 molar equivalents.

Examples of non-reactive polar solvents are dimethylformamide, dimethylacetamide and hexametapol (hexamethylphosphoric triamide), as well dimethyl sulphoxide.

Examples of alkali alcoholates of tertiary alcohols are, for example, potassium tert.-butylate and sodium tert.-amylate and other alkali metal alcoholates of other tertiary alkanols of, e.g., 1–12 carbon atoms. The exact amount of alcoholate employed is not critical.

The reaction can be conducted over a wide temperature range, e.g., from $-20°$ C. to the boiling point of the reaction mixture, preferably $0°$ to $50°$ C., more preferably about room temperature.

The dimethyl sulfonium methylide is preferably produced in situ by reacting the alkali alcoholate with trimethyl sulfonium iodide, e.g., by dissolving the starting $\alpha,\beta$-unsaturated polyketo steroid and suspending trimethyl sulfonium iodide in the reaction solvent and then gradually adding the alkali tert.-alcoholate to the resultant mixture to produce the dimethyl sulfonium methylide in situ. In this case, at least a molar equivalent of the alkali alcoholate, calculated on the starting steroid, whould be used to ensure complete reaction. An excess above this amount has no effect upon the course of the reaction.

The reaction product can be worked up in the usual manner, for example by precipitation, recrystallization, or chromatography.

The compounds producible according to this process are intermediates for the preparation of pharmacologically active compounds and intermediates useful in the production thereof, e.g., steroids having a methyl group and a hydroxy group on the same carbon atom by reductive opening of the oxirane ring. For example, $17\alpha$-methyltestosterone is obtained from $17\beta$-spiro-$1',2'$-oxiranyl-4-androsten-3-one by reductive opening of the ring, for example, with lithium aluminum hydride.

The well known aldosterone antagonist, 3-($7\alpha$-acetylthio-$17\beta$-hydroxy-3-oxo-4-androsten-$17\alpha$-yl)-propiolactone is obtained from spiro-$17\beta$-oxyranyl-4-androsten-3-one by the process according to U.S. Pat. No. 3,413,288 after enamination to give 3-($17\beta$-hydroxy-4-androsten-3-on-$17\alpha$-yl)-propiolactone, which itself is a biologically active compound (see, for reference, J.Am.Chem.Soc. 79 (1957) 4808; J.Org.-Chem. 24 (1959) 74; ibid. 24 (1959) 1109). This propiolactone is dehydrogenated in the 6-position (J.Org.-Chem. 24 (1959) 1109; U.S. Pat. No. 2,900,383) and treated with thioacetic acid according to German Published Application, DAS 1,121,610, for example.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

8.6 g. of 4-androstene-3,17-dione is dissolved in 65 ml. of dimethylformamide, and then 13.5 g. of trimethyl sulfonium iodide is added thereto. The thus-obtained suspension is combined with 25.5 g. of potassium tert.-butylate by adding the latter in small portions, so that the internal temperature does not exceed $25°$ C. The mixture is thereafter agitated for 4 hours at about $20°$ C. The thus-obtained reaction mixture is then introduced into 1 liter of ice water and stirred for 1 hour. The precipitated, crude spiro-$17\beta$-oxiranyl-4-androsten-3-one is vacuum-filtered, washed neutral with water, and dried, thus obtaining 8 g. melting, after recyrstallization from acetone/hexane, at $170°-173°$ C.

UV: $\epsilon_{240} = 15,600$. $[\alpha]_D = +132°$ (CHCl$_3$).

EXAMPLE 2

8.6 g. of 1,4-androstadiene-3,17-dione is dissolved in 65 ml. of dimethylformamide, and 13.5 g. of trimethyl sulfonium iodide is added thereto. To the thus-obtained suspension, 8.5 g. of potassium tert.-butylate is added in small portions so that the internal temperature does not exceed 20° C. The mixture is allowed to react further as set forth in Example 1 and then worked up. the thus-obtained crude spiro-17β-oxiranyl-1,4-androstadien-3-one is purified first by preparative layer chromatography (cyclohexane/ethyl acetate 1 : 1) and then by recrystallization from acetone/hexane, thus obtaining 4 g. of final product, m.p. 130°–132° C.

UV: $\epsilon_{244}$ = 14,800. $[\alpha]_D$ = +25° (CHCl$_3$).

EXAMPLE 3

8.6 g. of 4-pregnene-3,20-dione is dissolved in 65 ml. of dimethylformamide, and 13.5 g. of trimethyl sulfonium iodide is added thereto. 12.5 g. of potassium tert.-amylate is added in small portions to the thus-obtained suspension, so that the internal temperature does not exceed 30° C. The mixture is further reacted analogously to Example 1 and worked up. The crude 20,21-epoxy-20-methyl-4-pregnen-3-one is recrystallized from acetone/hexane, thus producing 6.5 g., m.p. 166° C.

UV: $\epsilon_{242}$ = 14,920. $[\alpha]_D$ = +100° (CHCl$_3$).

EXAMPLE 4

Analogously to Example 2, 4.3 g. of 1,5-androstadiene-3,17-dione in 32.5 ml. of dimethylformamide is reacted with 4.25 g. of potassium tert.-butylate and 6.75 g. of trimethyl sulfonium iodide. After working up and purifying the reaction product analogously, 2.1 g. of spiro-17β-oxiranyl-1,5-androstadien-3-one is obtained, m.p. 174°–182° C.

UV: $\epsilon_{226}$ = 11,100. $[\alpha]_D$ = +53° (CHCl$_3$).

EXAMPLE 5

Analogously to Example 1, spiro-11β,17β-dioxiranyl-4-androsten-3-one is obtained from 4androstene-3,11,17-trione.

UV: $\epsilon_{240}$ = 14,000.

EXAMPLE 6

Spiro-17β-oxiranyl-5α-androst-1-en-3-one is produced from 5α-androst-1-ene-3,17-dione analogously to Example 1.

EXAMPLE 7

In analogy to Example 1, spiro-3β-oxiranyl-5β-pregn-16-en-20-one is produced from 5β-pregn-16-ene-3,20-dione.

UV: $\epsilon_{240}$ = 7,900.

EXAMPLE 8

Spiro-17β-oxiranyl-4,6-androstadien-3-one is obtained analogously to Example 1 from 4,6-androstadiene-3,17-dione.

EXAMPLE 9

Analogously to Example 1, spiro-17β-oxiranyl-4-estren-3-one is produced from 4-estrene-3,17-dione.

EXAMPLE 10

From 19-nor-4-pregnene-3,20-dione, 20,21-epoxy-20-methyl-19-nor-4-pregnen-3-one is obtained analogously to Example 3.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of a α,β-unsaturated keto steroid having a spiro oxirane group from a polyketo steroid having an isolated keto group and an α,β-unsaturated keto group, the improvement which comprises reacting the polyketo steroid with dimethyl sulfonium methylide in a non-reactive polar solvent and in the presence of an alkali metal tertiary alcoholate.

2. A process according to claim 1, wherein the alkali metal alcoholate is sodium or potassium tertiary butylate or tertiary amylate.

3. A process according to claim 1, wherein the reaction solvent is dimethylformamide, dimethylacetamide or hexamethylphosphoric triamide.

4. A process according to claim 1, wherein the dimethyl sulfonium methylide is produced in situ by adding the alkali metal alcoholate to a mixture of the starting steroid dissolved in, and trimethyl sulfonium iodide suspended in the polar solvent.

5. A process according to claim 1, wherein the starting steroid is a 3,17-diketo or 3,20-diketo steroid wherein the 3-keto group is α,β-unsaturated.

6. A process according to claim 4, wherein the alkali metal alcoholate is sodium or potassium tertiary butylate or tertiary amylate.

7. A process according to claim 6, wherein the starting steroid is a 3,17-diketo or 3,20-diketo steroid wherein the 3-keto group is α,β-unsaturated.

8. A process according to claim 1, wherein the starting steroid is a steroid of the formula

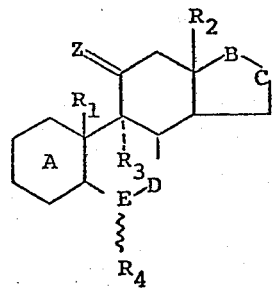

wherein A is

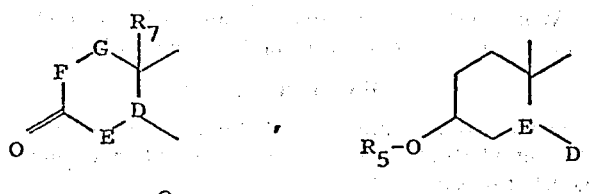

B-C is

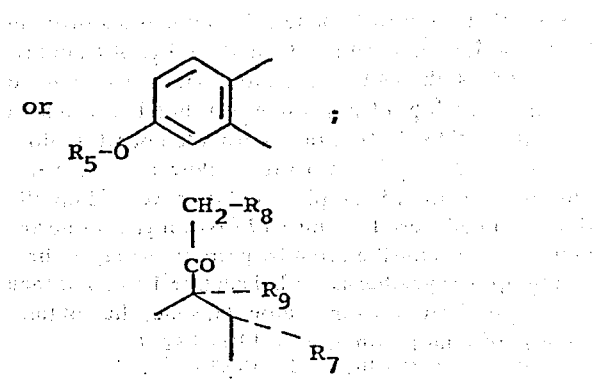

or

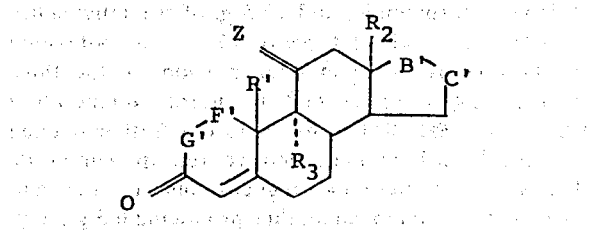

Z is an oxygen atom, two hydrogen atoms or the grouping H,OH; E-D is a single or double bond; F-G is

—$CH_2$—$CH_2$—,  —CH=CH,  —$CH_2$—CH($CH_3$)—,

—CH=C($CH_3$)— or —CH——CH—;
                          \    /
                           $CH_2$

R is a hydrogen atom or methyl; $R_2$ is methyl or ethyl; $R_3$ is a hydrogen, fluorine or chlorine atom; $R_4$ is a hydrogen, fluorine or chlorine atom or methyl; $R_5$ is a hydrogen atom or alkanoyl of up to 15 carbon atoms; $R_6$ is a hydrogen atom, methyl or ethinyl; $R_7$ is a hydrogen atom, methyl or -O-$R_5$; $R_8$ is a hydrogen atom, a halogen atom or -O-$R_8$; $R_9$ is a hydrogen atom or -O-$R_5$; $R_6$ and $R_7$ or $R_7$ and $R_9$ collectively are

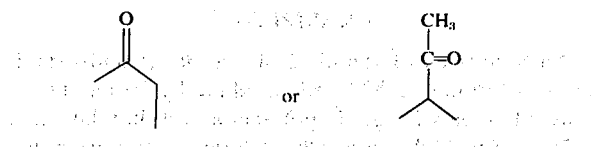

wherein $R_{10}$ and $R_{11}$ each are a hydrogen atom or alkyl of up to 5 carbon atoms, with the proviso that one of A and BC comprises a non-conjugated keto group and the other an α,β-unsaturated keto group.

9. A process according to claim 8, wherein the starting steroid is a steroid of the formula wherein B'C' is F' - G' is a single or double bond, and $R_1$, $R_2$, $R_3$, and Z each have the values given therein.

10. A process according to claim 9, wherein the alkali metal alcoholate is sodium or potassium tertiary butylate or tertiary amylate, and wherein the reaction solvent is dimethylformamide, dimethylacetamide or hexamethylphosphoric triamide.

* * * * *